US010281371B2

(12) United States Patent
Hong

(10) Patent No.: US 10,281,371 B2
(45) Date of Patent: May 7, 2019

(54) SEQUENTIAL AIR SAMPLER WITH FILTER CASSETTE MAGAZINE

(71) Applicant: Met One Instruments, Inc., Grants Pass, OR (US)

(72) Inventor: Seung-Ho Hong, Medford, OR (US)

(73) Assignee: Met One Instruments, Inc., Grants Pass, OR (US)

( * ) Notice: Subject to any disclaimer, the term of this patent is extended or adjusted under 35 U.S.C. 154(b) by 360 days.

(21) Appl. No.: 15/179,664

(22) Filed: Jun. 10, 2016

(65) Prior Publication Data

US 2017/0356825 A1 Dec. 14, 2017

(51) Int. Cl.
*G01N 1/22* (2006.01)

(52) U.S. Cl.
CPC .................. *G01N 1/2205* (2013.01)

(58) Field of Classification Search
CPC ........................ G01N 1/2205; G01N 1/2273
USPC .............. 73/863.01, 863.21, 863.23, 863.25; 96/413
See application file for complete search history.

(56) References Cited

U.S. PATENT DOCUMENTS

| 3,059,470 A * | 10/1962 | Baldwin ............ G01N 1/2202 55/422 |
| 3,540,261 A * | 11/1970 | Scoggins ............ G01N 1/2202 73/23.2 |
| 4,321,822 A | 3/1982 | Marple et al. |
| 4,439,100 A | 3/1984 | Fichtner et al. |
| 4,447,395 A | 5/1984 | Englar et al. |
| 4,552,285 A | 11/1985 | Luscher |
| 4,595,327 A | 6/1986 | Woodley |
| 4,834,944 A | 5/1989 | Wakatake |
| 4,886,412 A | 12/1989 | Wooding et al. |
| 5,075,079 A | 12/1991 | Kerr et al. |
| 5,165,521 A | 11/1992 | Schweitzer et al. |
| 5,386,318 A | 1/1995 | Kühnert et al. |
| 5,407,314 A | 4/1995 | Kempf |
| 5,898,114 A | 4/1999 | Basch et al. |
| 6,138,521 A | 10/2000 | Basch et al. |

(Continued)

OTHER PUBLICATIONS

Printout: Environmental Monitoring System, "Automatic dust sampling system to collect particular matter PM10 or PM2.4 or PM1", Type PNS 18T-3.1 DM / PNS 18T-6.1 DM, Comde-Derenda GmgH, Kieler Strasse 9, 14532 Stahnsdorf, Germany, Ed. Apr. 2015, 2 pages.

*Primary Examiner* — Robert R Raevis
(74) *Attorney, Agent, or Firm* — Thomas Schneck

(57) ABSTRACT

A sequential air sampler is provided having a rotatable carrier adapted to support filter cassettes received from a supply magazine at a load station, transport them to a sampling station where gas flow is directed through that cassette, and then be transported to an unload station to be received by a storage magazine. A Geneva driver operated by a single motor provides intermittent rotation to the carrier between fixed positions. A cam rotates in concert with the Geneva driver so that a follower in reciprocating motion pushes up and then pulls down a pair of plungers for simultaneous cassette loading and unloading whenever the carrier is at one of its fixed positions. Magazines have magnetically actuated stoppers to keep the stack of cassettes in place until released. Magazines may also have a retaining lid with a position-adjustable piston to secure cassettes for transport.

13 Claims, 21 Drawing Sheets

(56) References Cited

U.S. PATENT DOCUMENTS

| | | | |
|---|---|---|---|
| 6,164,489 A | 12/2000 | Altrock | |
| 6,167,767 B1 | 1/2001 | Mengel et al. | |
| 6,203,268 B1 | 3/2001 | Miyashita | |
| 6,244,117 B1 * | 6/2001 | Mengel | G01N 1/2273 435/30 |
| 6,309,362 B1 | 10/2001 | Guirguis | |
| 6,321,609 B1 | 11/2001 | Mengel et al. | |
| 6,497,319 B2 | 12/2002 | Atsumi et al. | |
| 6,881,579 B2 | 4/2005 | Hilson et al. | |
| 7,947,503 B2 | 5/2011 | Tuchman | |
| 8,011,260 B2 | 9/2011 | Scott et al. | |
| 8,119,065 B2 | 2/2012 | Bowers et al. | |
| 8,192,516 B2 * | 6/2012 | Yoon | B01D 46/0005 221/268 |
| 8,328,670 B2 | 12/2012 | Suko et al. | |
| 8,858,687 B2 | 10/2014 | Jackson | |
| 9,032,780 B2 | 5/2015 | Anderson et al. | |
| 2006/0261207 A1 | 11/2006 | Woodruff et al. | |
| 2012/0261629 A1 | 10/2012 | Andkjar | |
| 2016/0054204 A1 * | 2/2016 | David | G01N 1/2205 73/863.23 |

* cited by examiner

SEQUENTIAL AIR SAMPLER WITH FILTER CASSETTE MAGAZINE

TECHNICAL FIELD

The present invention generally relates to a method and apparatus for sequential air sampling devices for collecting particulate matters and chemical species in the air and other gases. More specifically, this present invention relates to sample filter cassette magazines and automatic filter cassette transfer methods and apparatus.

BACKGROUND ART

In order to protect public health, the United States Environment Protection Agency (EPA) has developed air sampling protocols, including a standardized air sampling system. Under such EPA protocols, in order to collect a series of daily samples a site operator needs to be at an air monitoring site that is equipped with a single event air sampler every day so as to retrieve the sample-loaded filter and install a new filter.

To minimize inconvenience, many monitoring sites have accommodated sequential air samplers. Currently most sequential samplers use a linear transfer movement mechanism to move successive filter cassettes from a clean filter cassette magazine station to a sampling station and finally to a storage magazine station. For this sequential movement, a filter cassette carrier moves forward and backward by precisely controlled actuators.

Some systems use several electric linear actuators, stepper motors with belt, or pneumatic actuators to achieve this linear movement. Therefore, these systems often require an accurate control system to correctly position the carrier.

One broadly available EPA designated sequential air sampler uses a pneumatic actuator and solenoid actuators to move filter cassette from position to position. To activate the pneumatic actuators, lots of complex pressurized air tubes are linked with valves and other control systems. Therefore, the biggest drawback of this system is maintaining leak-free complex pneumatic system. If a malfunction occurs, it would require a lot of time and effort to find the source(s) of the malfunction.

U.S. Pat. No. 5,898,114 to Basch et al. uses a multi-filter cassette carrier for a sequential air sampler. In U.S. Pat. No. 6,138,521 to Basch et al., the cassette magazines are installed beneath the transfer mechanism. Therefore, it requires a filter cassette lifting mechanism at the supply station and also requires a drop preventing aperture at the storage magazine station. This system uses a pneumatic actuator and couple of solenoid actuators to move filter cassette from position to position, and therefore require precise pneumatic and sequential control and frequent maintenance.

The system in U.S. Pat. No. 8,192,516 to Yoon et al. uses two step motors, one for moving filter cassettes from station to station and another for moving the filter cassette vertical position. This system also requires precise position control to locate the filter cassette at right positions.

U.S. Pat. No. 6,167,767 to Mengel et al. uses a Geneva drive for indexing sampler position.

SUMMARY DISCLOSURE

A sequential air sampler is provided which has an automatic rotating filter cassette transfer mechanism with magnetic force driven sample filter cassette magazines to hold multi-stacking filter cassettes in one magazine. All mechanisms of the sequential air sampler move the filter cassette from place to place by use of a Geneva drive, roller follower and cam, lever systems, etc. In particular, the filter cassette moving mechanism simultaneously moves an unloaded clean filter from its supply magazine to the sampling station, and a sample-loaded used filter cassette from the sampling station to a storage magazine station by means of a Geneva driver. A roller-cam mechanism, which rotates together with the Geneva driver, simultaneously pushes up both sampling station and storage magazine station plungers. After the sampling process is finished, the same roller-cam mechanism pulls down both plungers to the lower position. All of these sequential movements operate by a single gear-motor.

The filter cassette magazine has a stopper which prevents the stack of filter cassettes from dropping out of the magazine until a filter cassette from the stack is specifically released onto the filter cassette carrier, e.g. by using magnets to move a stopper. In that case, the stopper, which is connected at the end of a rod spring, moves outward by magnetic force to release filter cassette(s) at the supply magazine station from the filter cassette magazine onto the carrier. At the storage magazine station, the filter cassette stopper holds sample loaded filter cassettes stacked in safe position.

A reflectance sensor may be used to detect the presence of filter cassettes in the system. The sequential sir sampler can easily be adapted to accommodate taller filter cassettes (or multi-filter loaded filter cassettes) by replacing spacers between the Geneva drive plates with taller spacers.

ADVANTAGES

The present invention uses only one motion power source (gear motor) to move filter cassettes from station to station, and it all happens simultaneously. Both the sealing of a new filter from the filter cassette supply magazine for sampling at the sampling station and the storing of the used filter cassette in a filter cassette storage magazine occur simultaneously after filter cassette movement by the same gear motor. The Geneva drive mechanism's intermittent or stepping rotation allows precise positioning of filter cassettes, and associated cam wheels have adequate dwelling period, so that the system doesn't require any accurate electronic positioning system(s).

The filter cassette magazines have minimal parts (and no moving parts) compared to contacting neighborhood part (s)-like systems (cf. U.S. Pat. Nos. 8,192,516 and 6,138,521). A filter cassette stopper in the filter cassette magazine has adequate free space around the stopper, which keeps it free of jamming. Moreover, a reflectance sensor may be used to sense the presence of a filter cassette and prevent any malfunction. But, if necessary (such as during a sudden power outrage or a malfunction situation), an operator can still easily recover a filter cassette manually simply by lifting a top station holding plate of the transport system.

DETAILED DESCRIPTION

Figure 1:
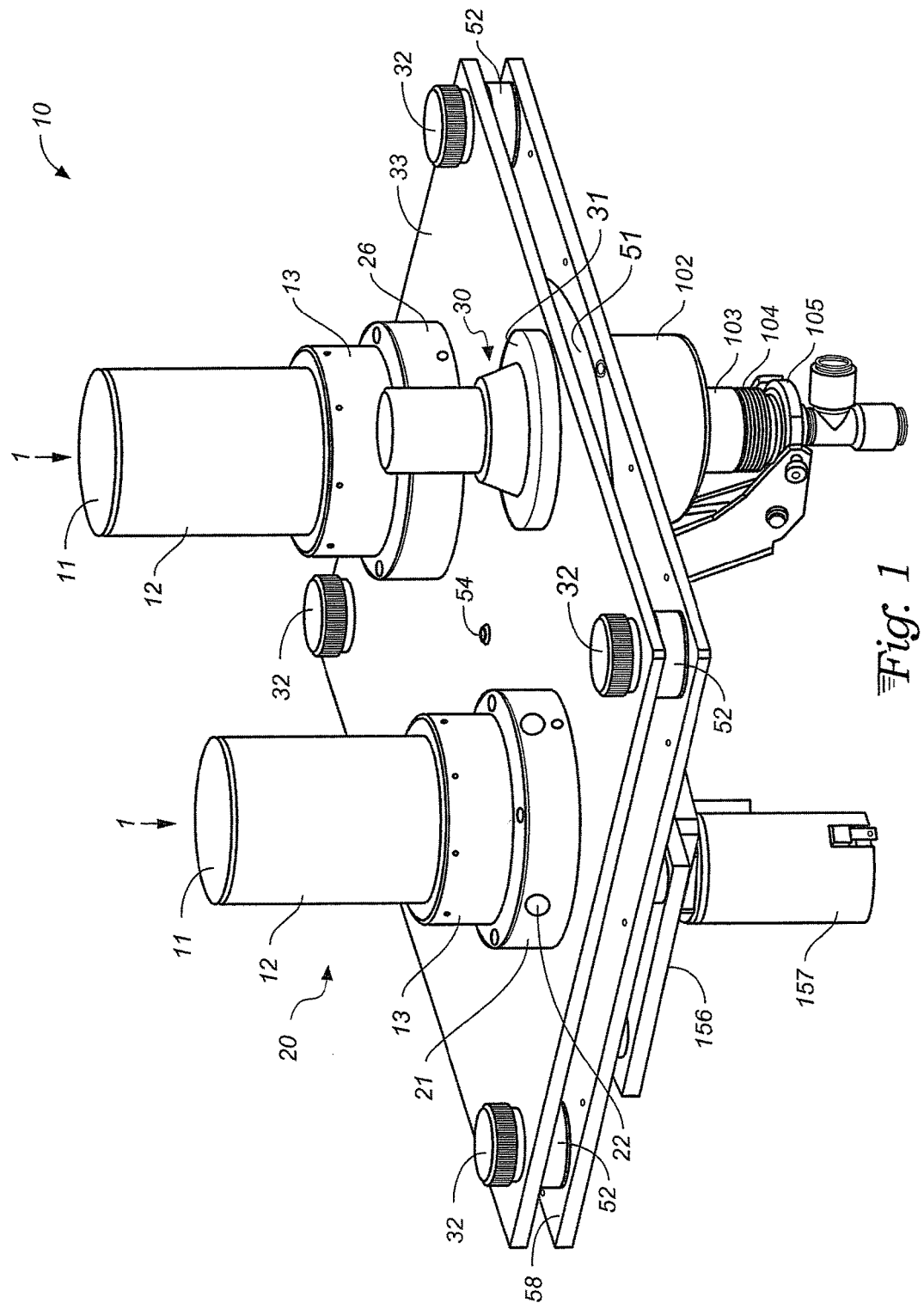
FIG. 1 is top perspective view of a sequential air sampler in accordance with the present invention.

FIG. 1 shows a sequential air sampler having a filter cassette supply station 20, a sampling station 30, and a filter cassette storage station 10. All these three stations are sitting on top of a station holding plate 33. The center of each station is located the same distance from a Geneva drive output shaft 54. A supply station filter cassette magazine 1 is sitting at the supply station 20 inside of a supply station mounting index 21. The supply station mounting index 21 has four magnets 22 at four equally spaced locations around its radial direction.

The magnets 22 pull filter cassette stoppers 15 (seen in FIG. 10) in an outward direction and let a clean filter cassette F1 drop into a hole 63 (seen in FIG. 3) of an intermittently rotating filter cassette carrier 51.

A storage station filter cassette magazine 1 is sitting at the storage station 10 inside of a storage station mounting index 26. The inside mounting index 26 has four ball plungers 27 (seen in FIG. 3) on top of the station holding plate 33. The station holding plate 33 is secured with four fasteners 32 on top of four spacers 52.

Figure 2:
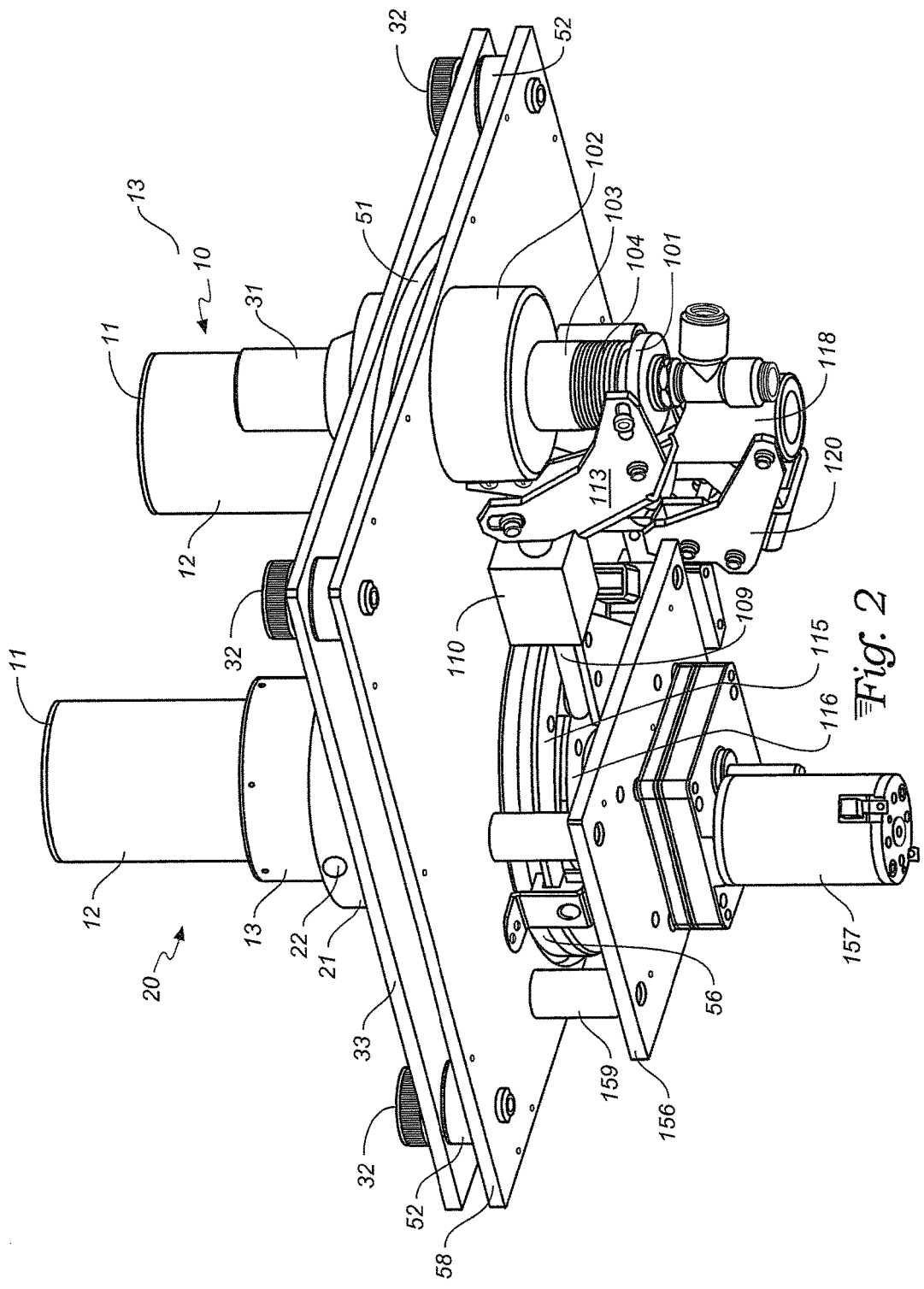
FIG. 2 is bottom perspective view of sequential air sampler in accordance with the present invention.

Referring to FIG. 2, from a bottom perspective it can be seen that a gear motor 157 rotates a Geneva drive input wheel 56 with outer cam 115 and inner cam 116. The outer cam 115 and inner cam 116 move a roller follower 109 back and forward along the guide block 110. Lever systems 113 and 120, connected at the end of roller follower 109, turn the horizontal movement of the roller follower 109 and sliding rod 124 (see FIG. 3) into vertical movement of a sampling station plunger 103 and a storage station plunger 118.

Figure 3:
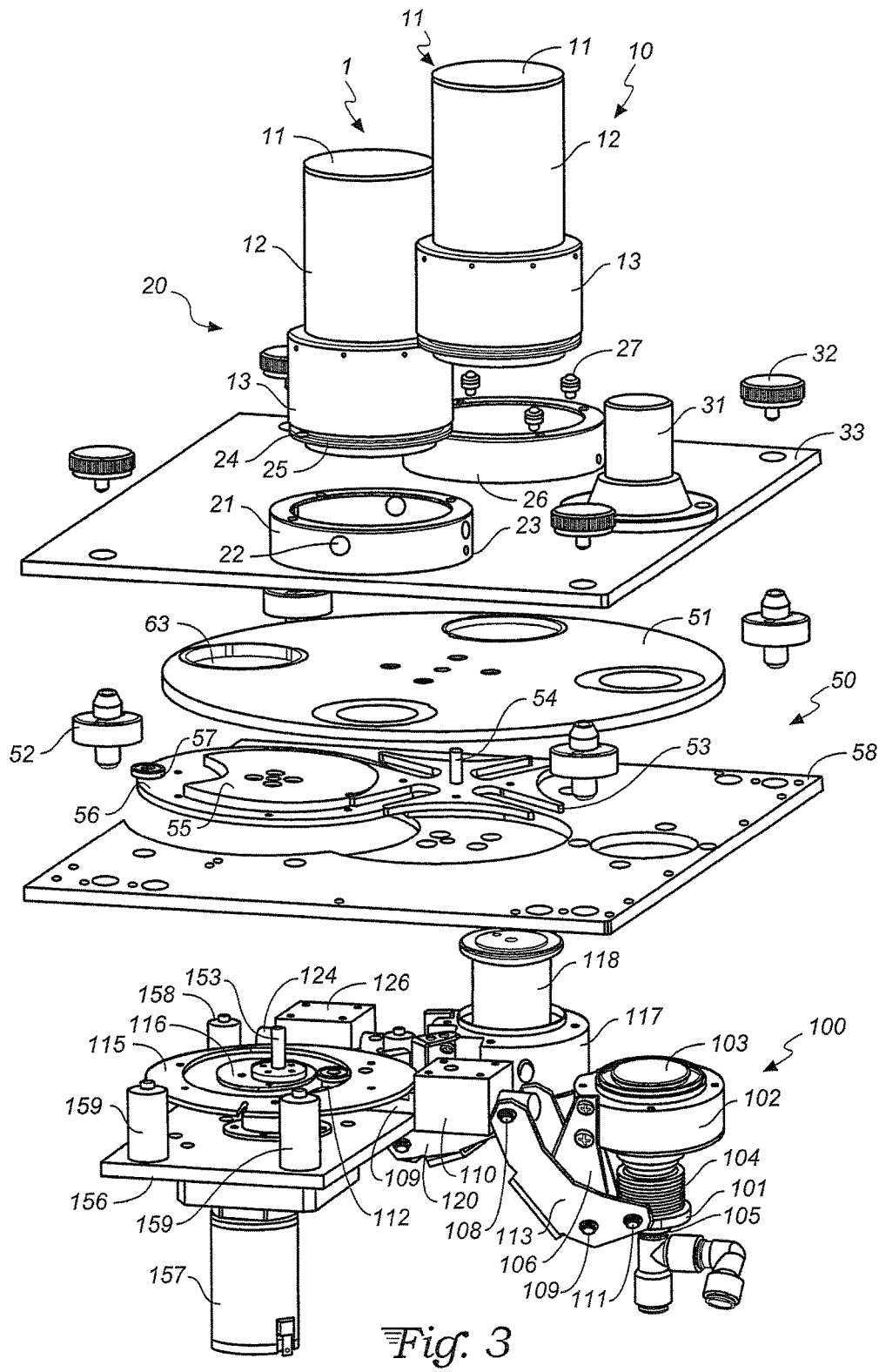
FIG. 3 is an expended perspective view of sequential air sampler in accordance with the present invention.

FIG. 3 shows an exploded perspective view of the sequential air sampler and in particular shows how each of the parts are connected to each other. A plunger moving mechanism 100 includes mainly a gear motor 157, cams 115, 116, a roller follower 109, and lever systems 113, 120, as well as the plungers 102, 118 themselves and other related supporting parts. All parts of the plunger moving mechanism 100 are attached underneath of the lower plate 58. The shaft of the gear motor 157 is directly connected with the Geneva drive's input shaft 153. Shaft 153 rotates the Geneva drive input wheel 56, as well as the inner-cam 116 and outer-cam 115. Inner-cam 116 and outer-cam 115 drive the roller follower 109 in a reciprocating motion back and forth horizontally along a guide block 110. The other side of the roller follower 109 is connected with a sampling station 30 lever system 113. The purpose of the lever system 113 is to transfer horizontal movement of roller follower 119 into vertical movement of a sampling station plunger 103. The effort distance between the pins 107 and 108 is longer than the resistance distance between the pins 107 and 111. Lever system 113 reduces roller follower 109 travel distance to sampling station plunger 103 travel distance, which is the same as the ratio of resistance distance to effort distance.

A sliding rod 124 is directly connected to the roller follower 109 by a connecting plate 125 and slides the same distance as the roller follower 109. Sliding rod 124 moves the storage station plunger 118 up and down by means of the lever system 120. Lever system 120 amplifies the roller follower travel distance 136 as the ratio of effect and resistance distance of lever system 120.

The Geneva drive filter cassette transfer mechanism 50 includes a Geneva drive input wheel 56, a locking wheel 55, a Geneva drive output wheel 53, and a filter cassette carrier 51. This mechanism 50 converts continuous rotary motion of Geneva drive input wheel 56 into intermittent or stepped rotary motion of Geneva drive output wheel 53 between a set of four fixed rotational positions of the carrier that are equally spaced 90 degrees apart. The Geneva drive input wheel 56 and locking wheel 55 are mechanically attached along with a shaft 153. One rotation of Geneva drive input wheel 56 makes one-fourth rotation of Geneva drive output wheel 53. The filter cassette carrier 51 also rotates one-fourth of a revolution, along with the Geneva drive output wheel 53. The filter cassette carrier 51 has four holes 63 at equal 90 degree angle spacing.

The Geneva drive filter cassette drive mechanism may be secured by two plates 33 and 58 with four fasteners 32 and with four spacers 52. The top plate 33 accommodates the supply magazine station 20, the sampling station 30, and the storage magazine station 10.

Figure 4:
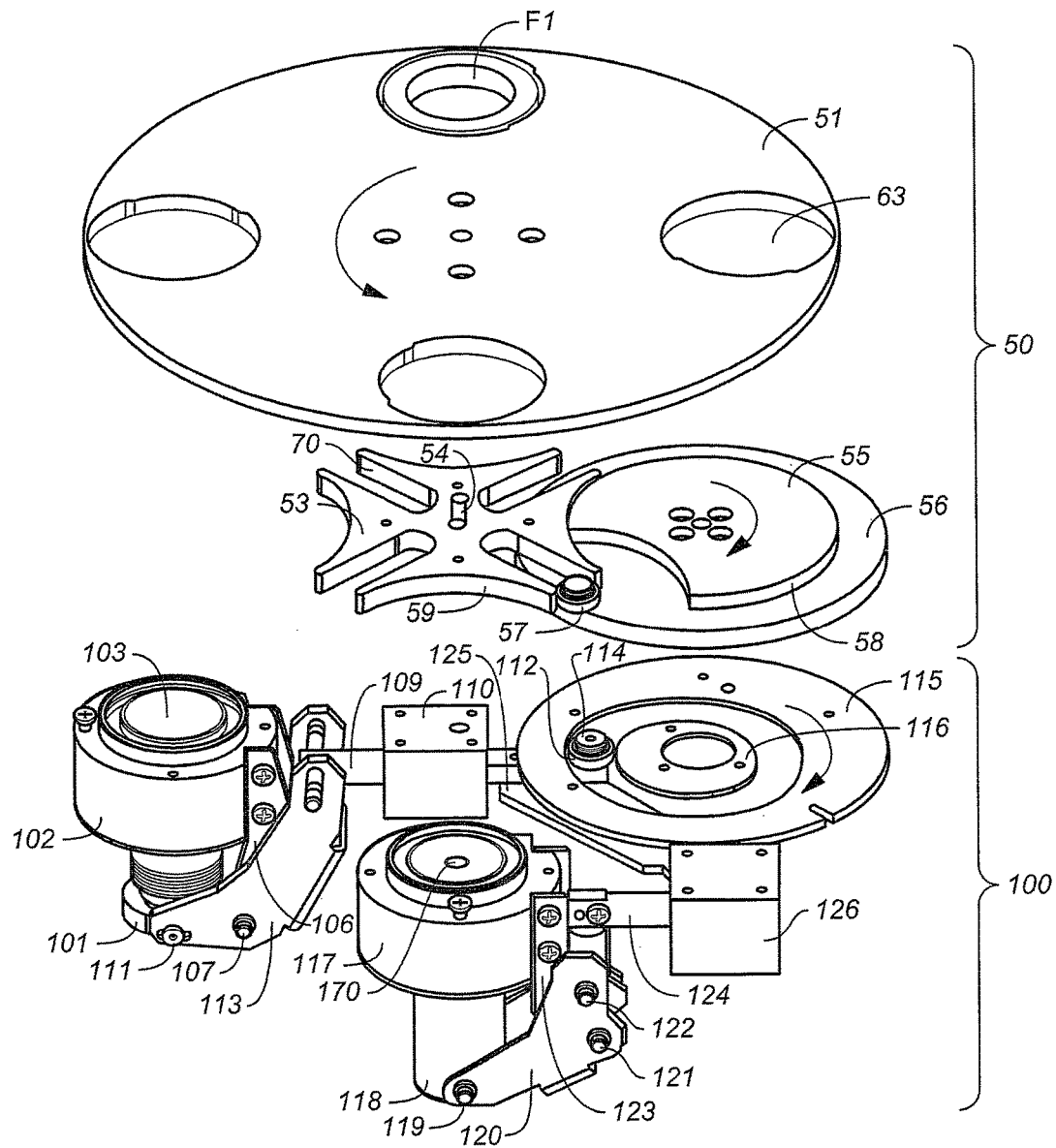
FIGS. 4, 5 and 6A are partial expended perspective views of filter cassette moving mechanism with three different positions.
Figure 5:
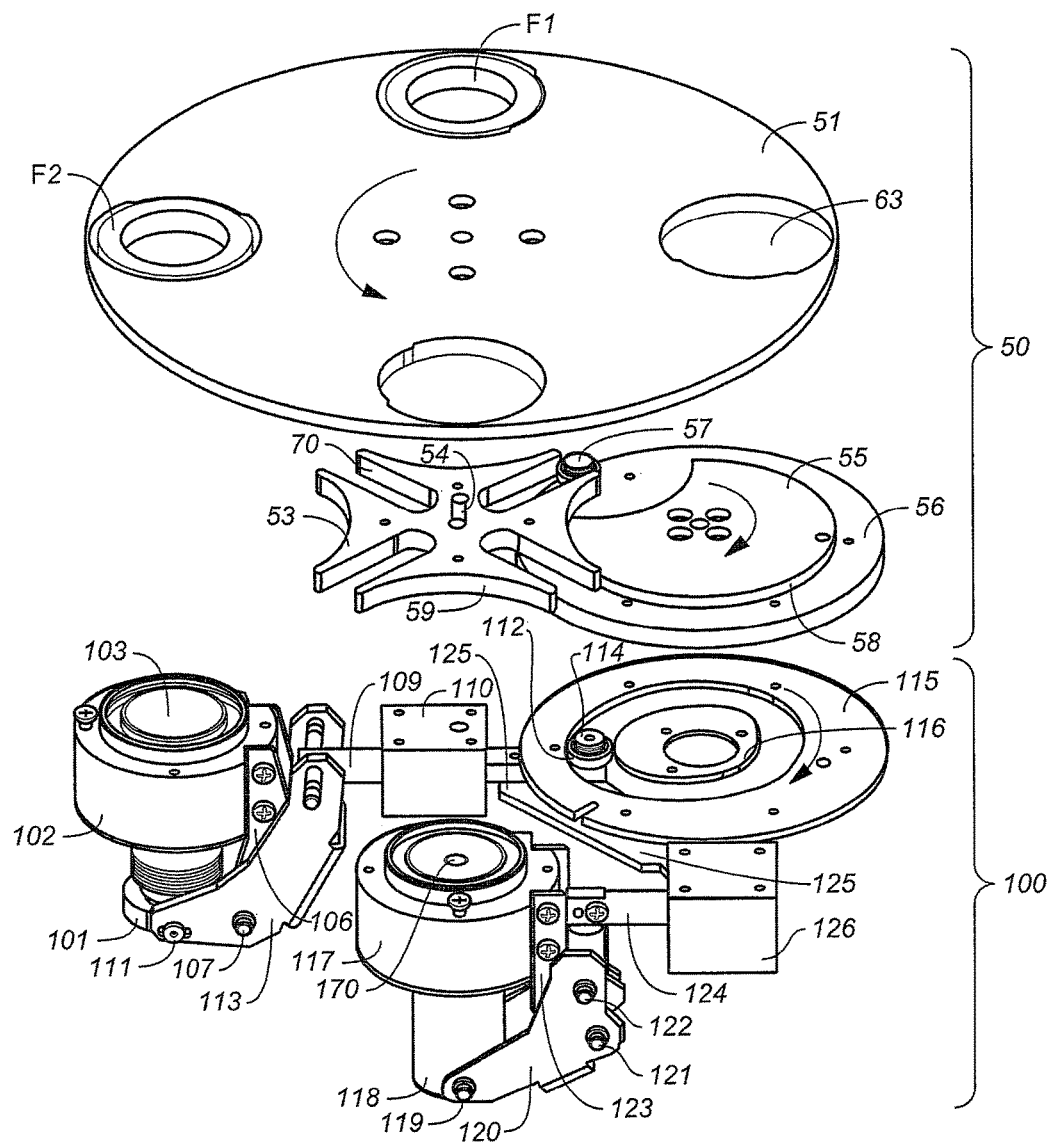

FIGS. 4, 5 and 6 show the operational steps of the sequential air sampler. In the operation of Geneva drive filter cassette transfer mechanism 50, when the Geneva drive input wheel 56 is rotated by a gear motor 157 (see FIG. 3) in a clockwise direction, a ball bearing 57 is received in one of the radial slots 70 of the Geneva drive output wheel 53 and engages the side wall of such slot to rotate the Geneva drive output wheel 53 in a counterclockwise direction. When the Geneva drive input wheel 56 rotates a first 90 degree angle with uniform angular speed, the Geneva drive output wheel 53 also rotates a 90 degree angle in the opposite direction with differential angular velocity. Simultaneously, the filter cassette carrier 51 moves a new filter cassette F1 in the supply magazine station 20 (see FIG. 3) to the sampling station (see FIG. 3). When the new filter cassette F1 is in the sampling station position, another new filter cassette at the supply magazine station 20 is dropping from the filter cassette magazine 1 into the next filter cassette carrier hole 63 and then waits until the next turn of the carrier. The outer cam 115 and inner cam 116 also rotate with the Geneva drive input wheel 56 simultaneously as well as filter cassette carrier 5 (see FIG. 5). During the first 90 degree rotation 133 of inner-cam 116 and outer-cam 115, the roller follower follows cam profile line, "dwelling period" 131 (see FIG. 7) and stay without linear movement.

Figure 6A:
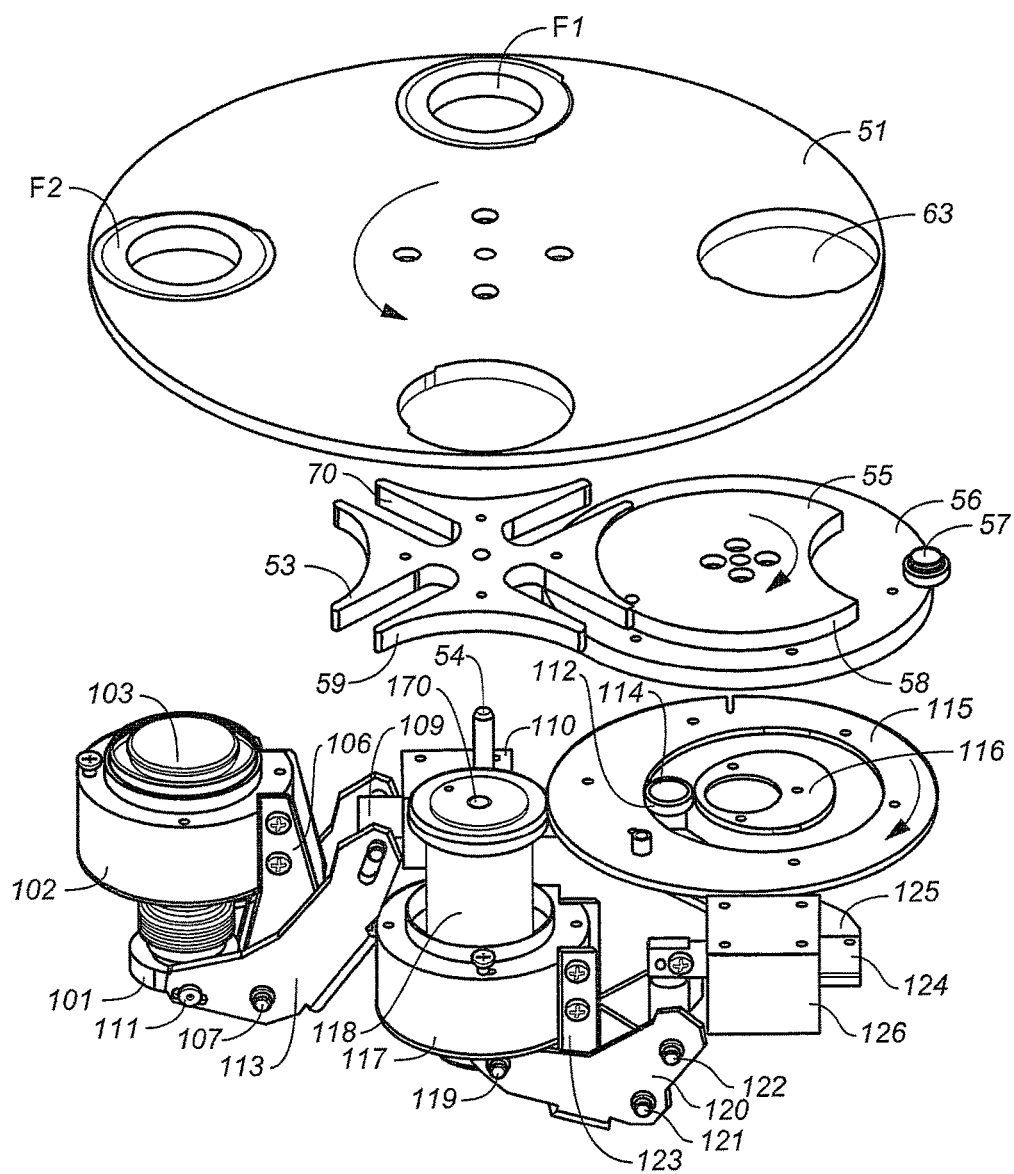

After ball bearing 57 slips out from the radial slot 70, the peripheral surface 58 of locking wheel 55 engages with concave surface of Geneva drive output wheel 53 and secures rotational movement until ball bearing 57 slips in next radial slot 70 or 270 degree rotation (see FIG. 6A). After a 90 degree turn of the Geneva drive input wheel, the guide bearing 112 slides along with outer cam profile line 131 and moves the roller follower slides toward to rotating center of cams 115, 116 until next 130 degree of rotation (see FIG. 7). At this potion, the roller follower 109 moves lever systems 113, 120 and pushes up sampling station plunger 103 and storage station plunger 118 to its own highest position.

Figure 6B:
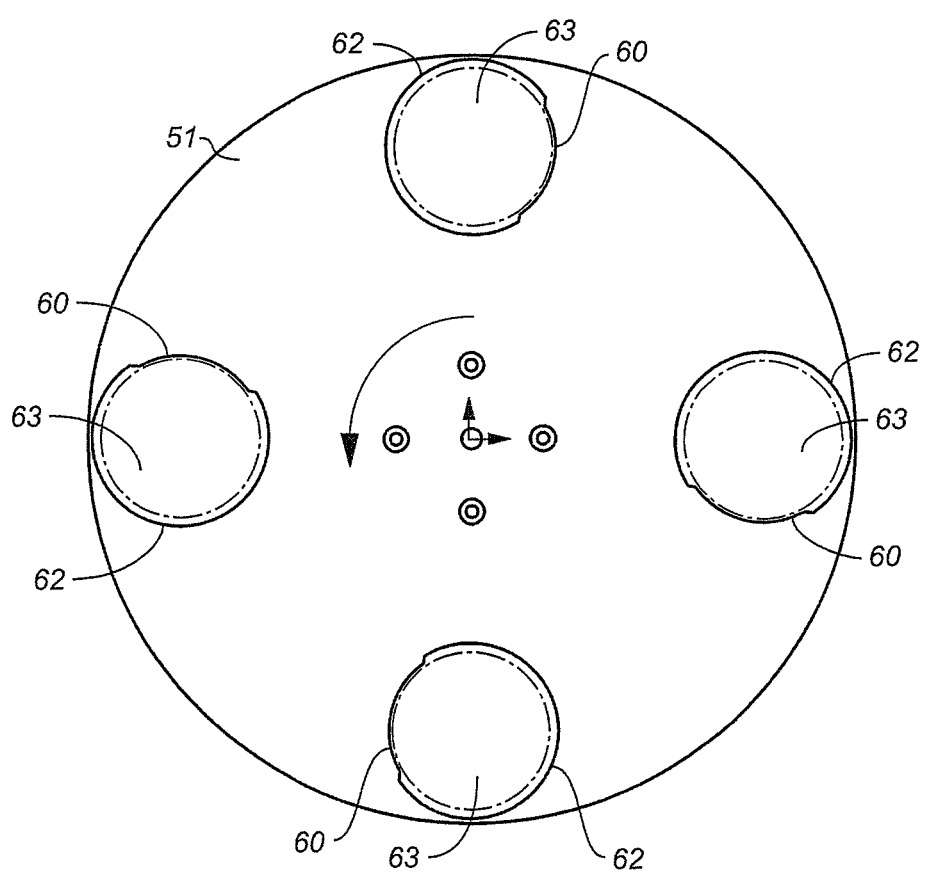
FIG. 6B shows open hole shape in the filter cassette carrier.

FIG. 6B shows four open holes 63 in the filter cassette carrier 51 forming receptacles for the filter cassettes. The radius 60 is same as a filter cassette and the adjusted radius 62 is larger than filter cassette radius. The radius 62 is big enough to prevent any squeezing of filter cassette when it is dropped from the filter cassette magazine 1. The radius 60 is located right side or back side of filter cassette 51 rotation direction. Filter cassette is moving against surface having radius 60 to position same as the center of sampling station 30 and storage station 10.

Figure 7:
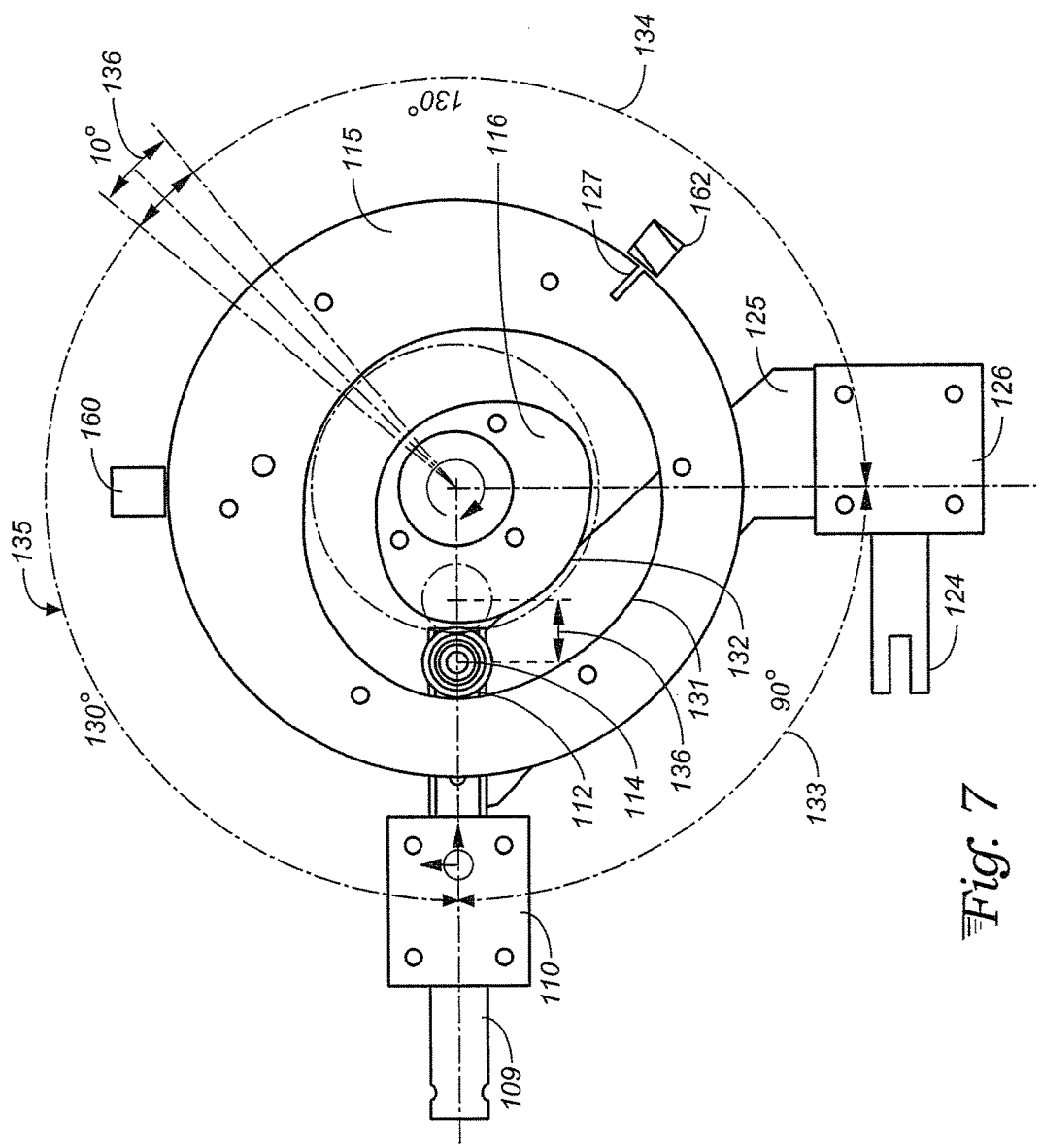
FIG. 7 shows roller follower and cam elevational view which change rotational movement to linear movement to drive plungers up and down.

With reference to FIG. 7, which shows an illustrative embodiment of the roller slide 109 and operation of the cams' 115, 116, there is seen to be two cam plates, an inner cam 116 and an outer cam 115. A guide bearing 112 attached at one end side of the roller follower slides along with cam-profile 131, 132 and converts rotation movement of cams 115, 116 to linear motion of the roller follower 109. Cams 115 and 116 have three cam-profile sections 133, 134 and 135. Whenever the guide bearing 112 is in a dwell period 133, the roller follower will stay still. At this period of rotation, Geneva drive input wheel 56 rotates the filter cassette carrier by 90 degrees and brings a new filter cassette F1 from the supply magazine station 20 to the sampling station 30 (see FIG. 3). After another 90 degree rotation, the roller follower 109 slides toward the cams 115 and 116 until next 130 degree of cam rotation 134. The next 10 degree angle 136 is another dwell period. The roller follower 109 moves a sampling station lever system 113 and sliding rod 124 connected directly with roller follower 109 by connecting plate 125. The sliding rod 124 moves a storage station plunger 118 up and down. When a sensor 162 indicates slot 127, it expresses that two plungers 103, 118 are in the lowest position and a ball bearing starts engaging with radial slot 70. When a sensor 160 indicates slot 127, it expresses that the two plungers 103, 118 are in their highest position and ready for an air sampling process.

Figure 8:
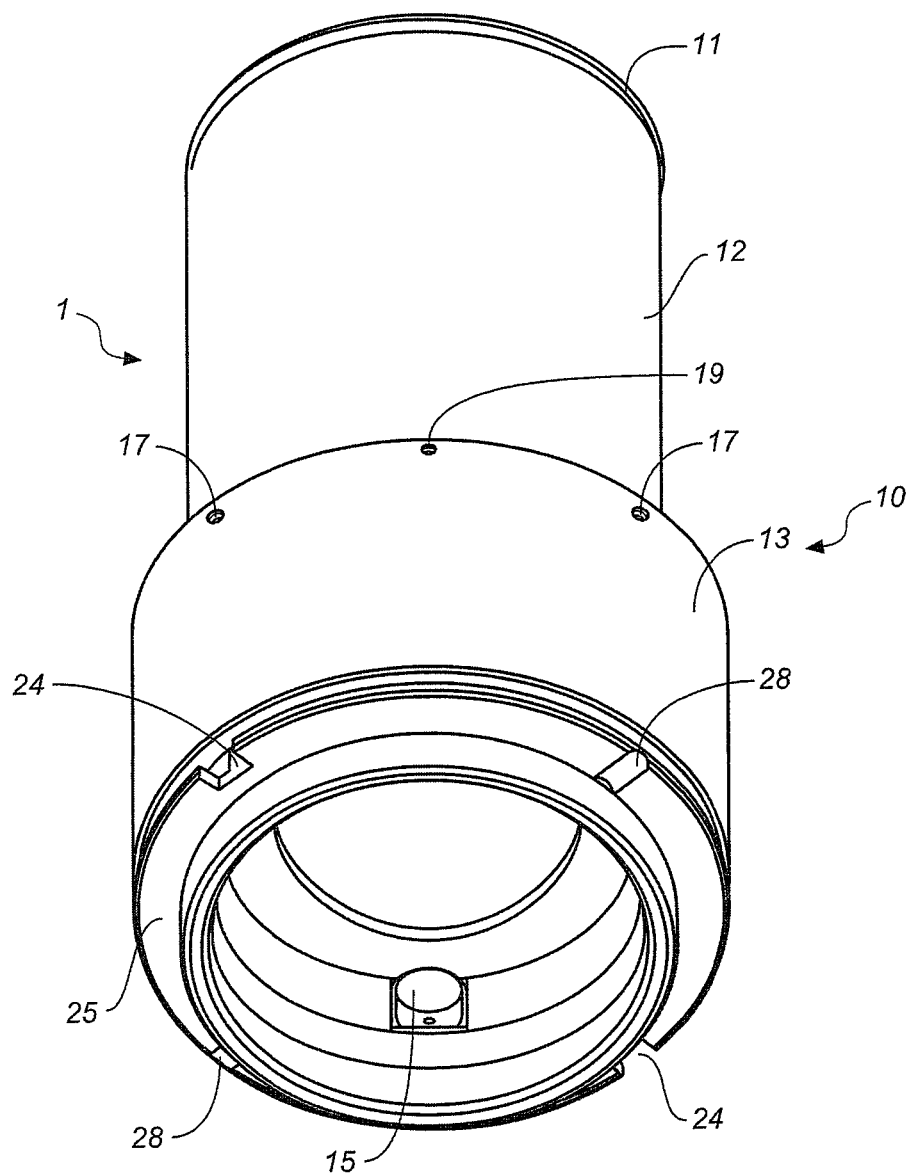
FIG. 8 is a bottom perspective view of filter cassette magazine.
Figure 9:
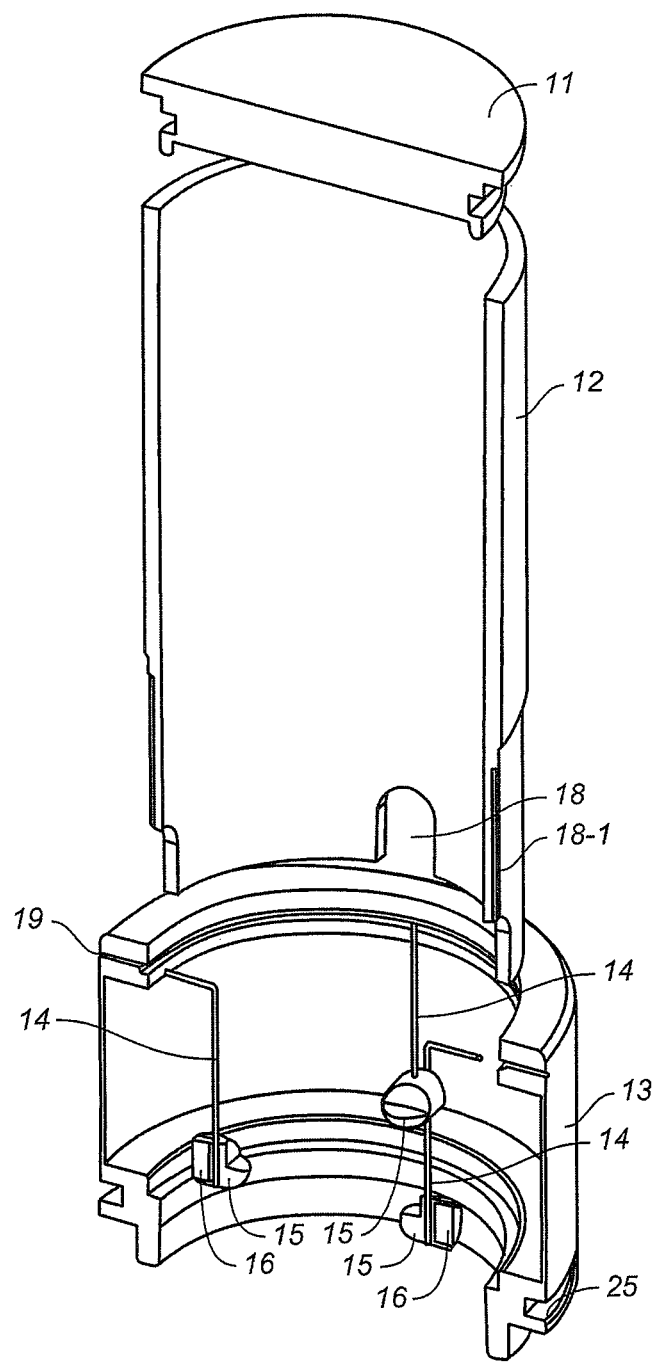
FIG. 9 is a cross-cut view of expended filter cassette magazine.

Referring to FIGS. 8 and 9, as seen from respective bottom perspective and exploded cross-sectional perspective views of the filter cassette magazine 1, the filter cassette magazine includes a lid 11, a magazine tube 12, and a tube holder 13. The magazine tube 12 is coupled with the tube holder 13 and secured with four set screws 17. The tube holder 13 has two mounting slots 24 to engage into a supply mounting index 21 and a storage mounting index 26. The tube holder 13 also has two settle groves 28 for positioning a filter cassette magazine when engaged with storage side mounting index 26 (see FIG. 8). The magazine tube 12 has four rounded slot holes 18 at the bottom with equal space. The slot hole 18 accommodates a filter cassette stopper 15 (see FIG. 9). Each tube holder accommodates four filter cassette stoppers 15. The filter cassette stopper 15 is attached at the end of rod spring 14 with magnet 16. The bended part of other end of rod spring 14 is goes into a hole 19 and a recessed narrow slot 18-1 secures the rod spring 14 from swinging in a peripheral direction. The portion of the filter cassette stopper extending inside of the magazine tube 12 has two different shapes: a bottom round part and a top flat part.

Figure 10:
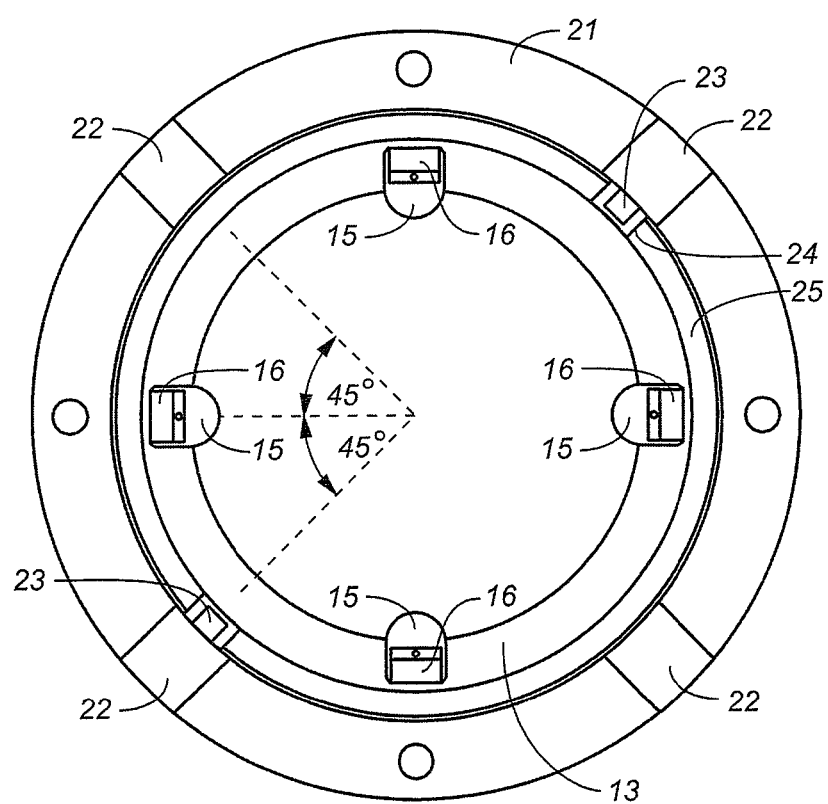
FIG. 10 shows illustrative embodiment of filter cassette stopper and filter cassette magazine supply station 20 mounting index 21.
Figure 11:
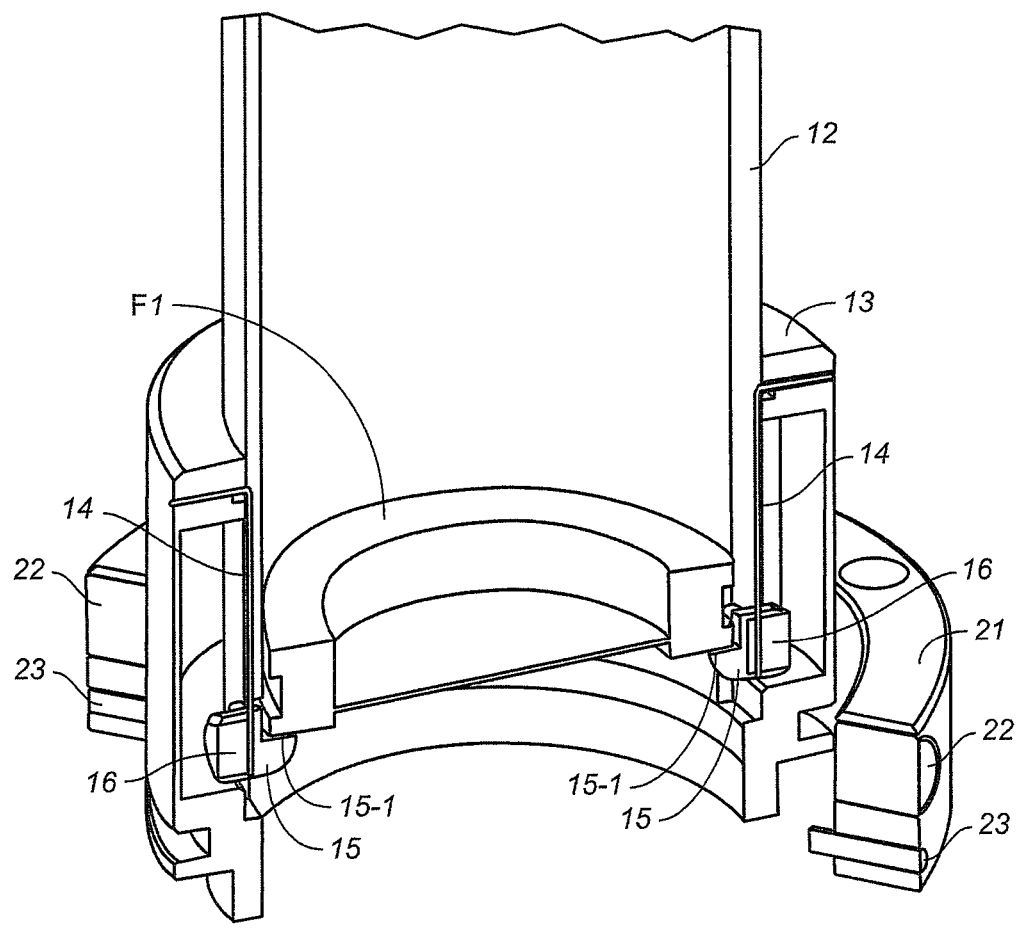
FIG. 11 shows illustrative embodiment of operation of the filter cassette stopper part.
Figure 12:
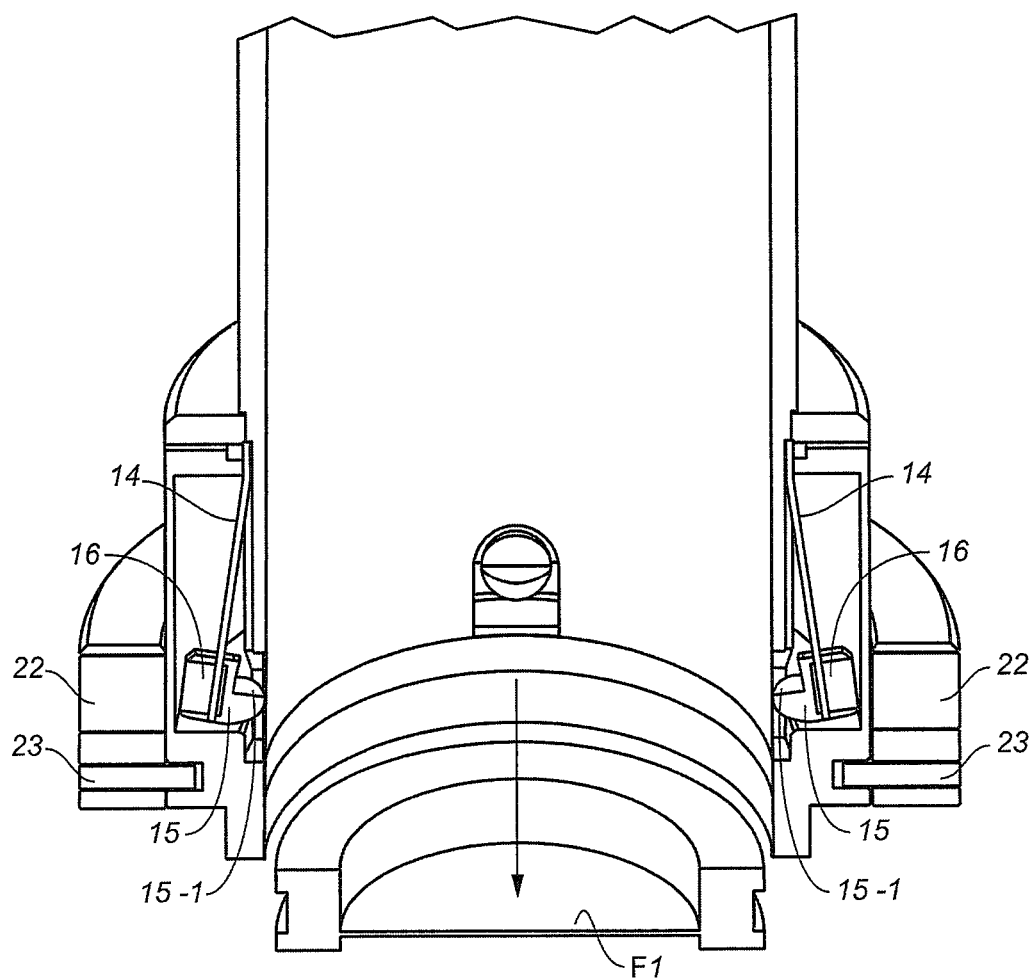
FIG. 12 shows illustrative embodiment of filter cassette drop induced by magnetic reaction.
Figure 13:
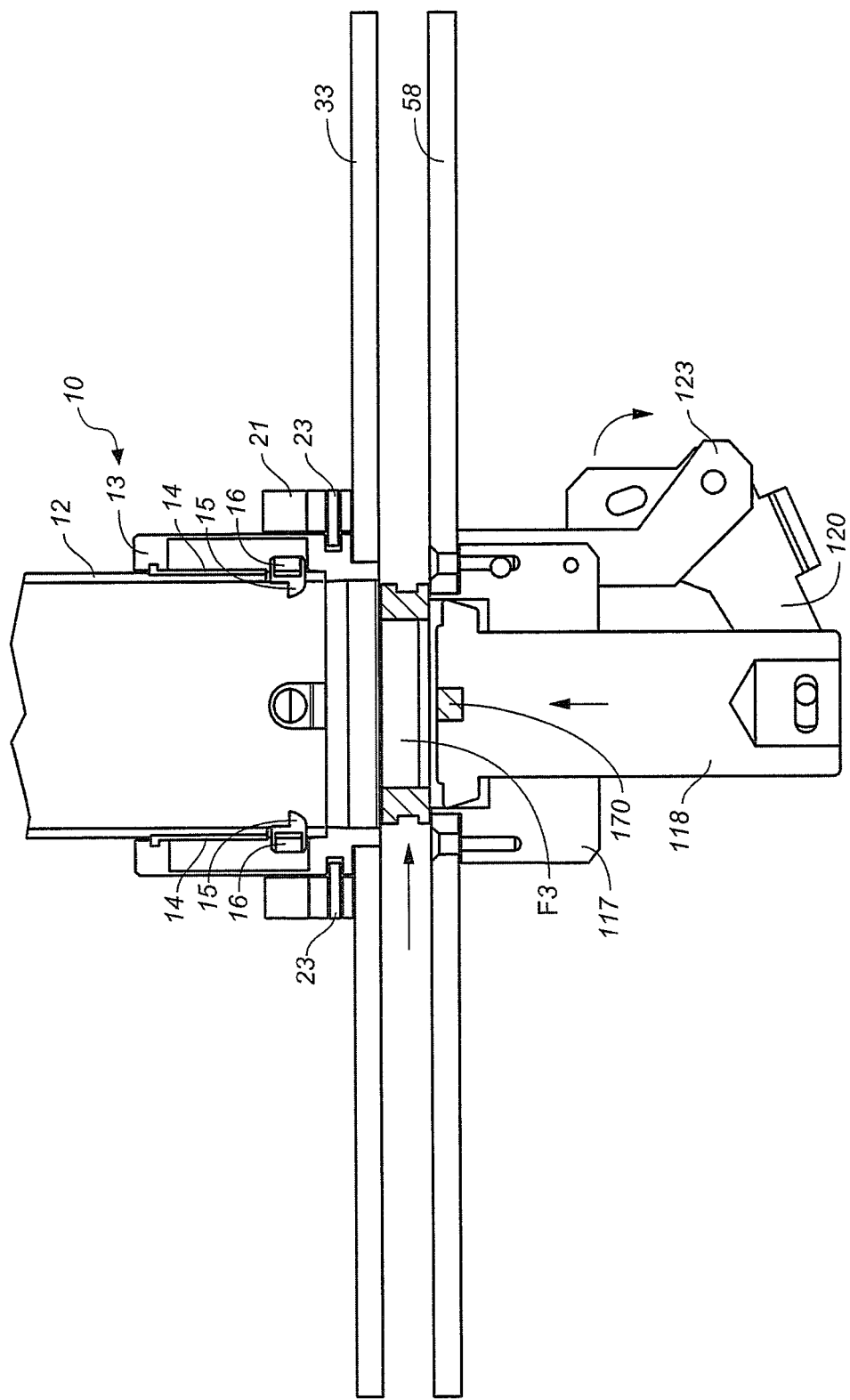
FIG. 13 through 16 show e filter cassette storage processes.
Figure 14:
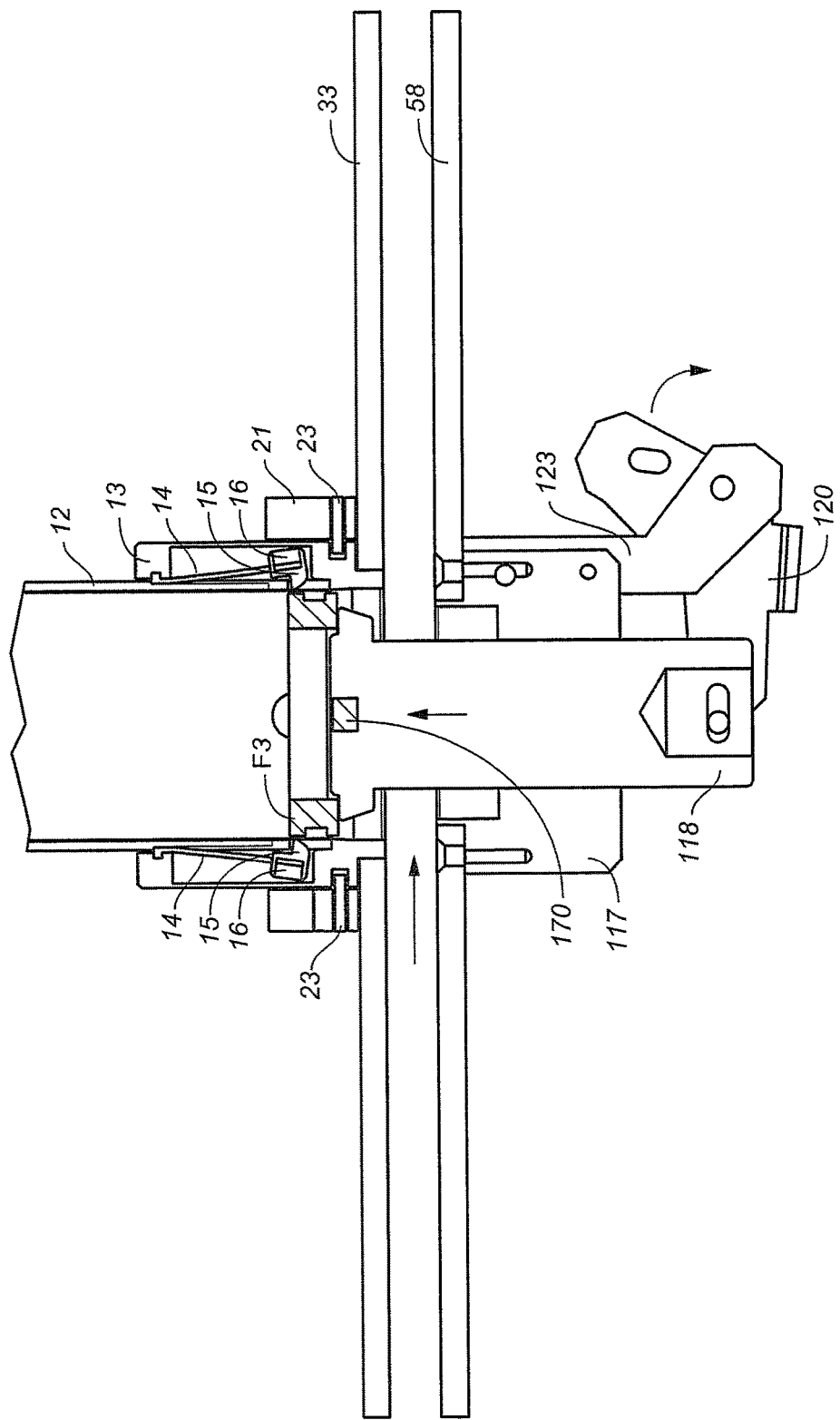
Figure 15:
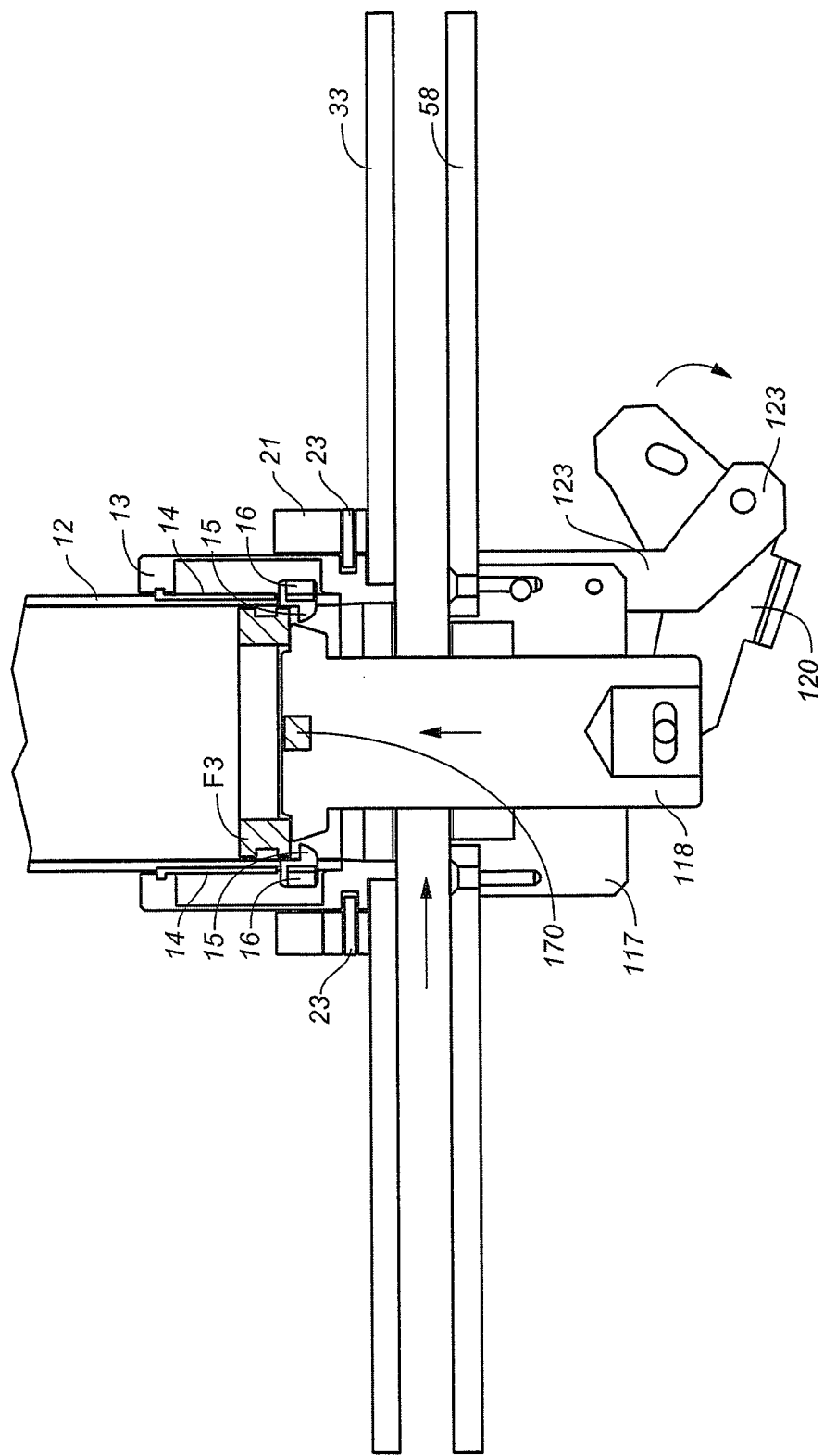
Figure 16:
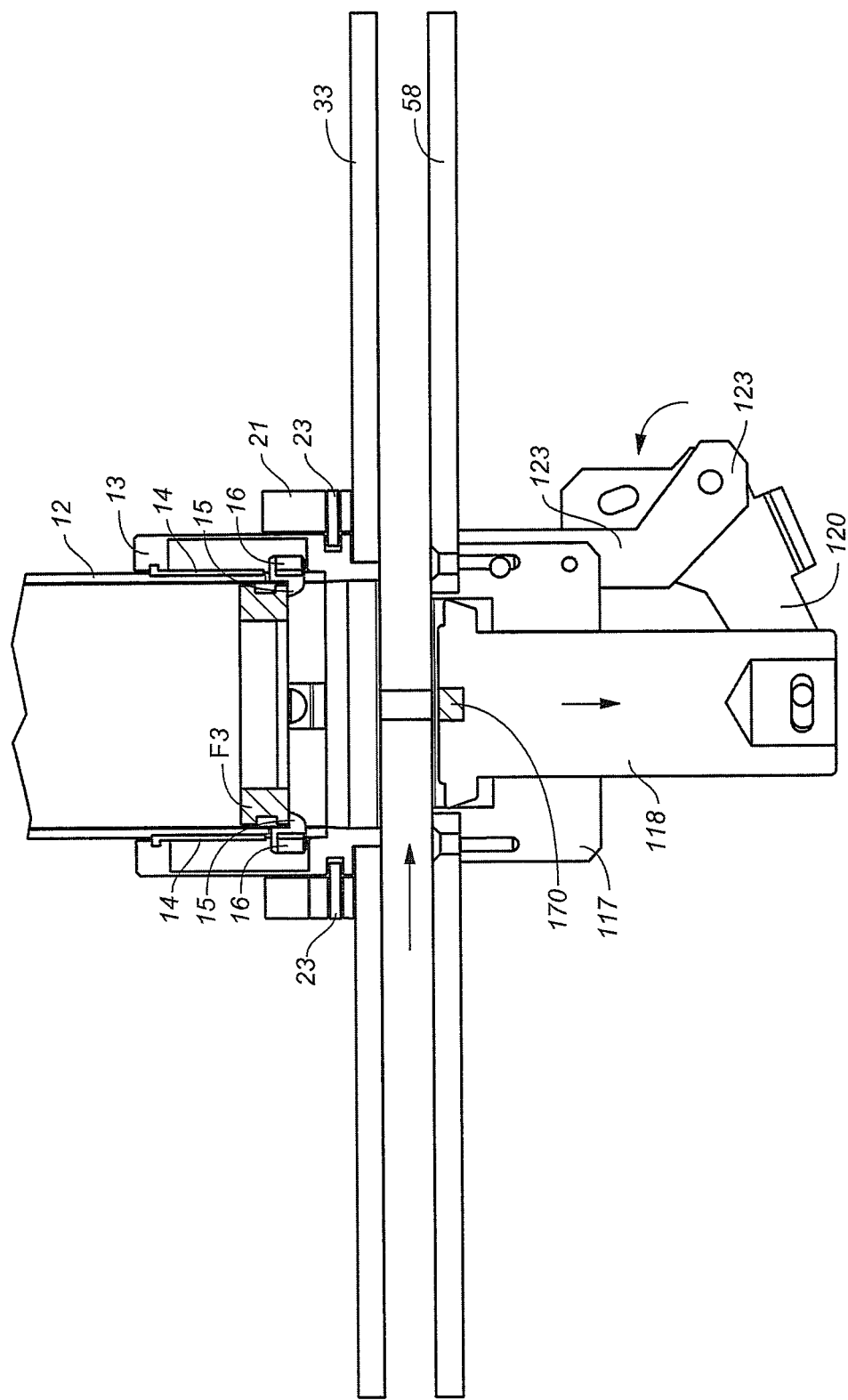

FIGS. 10, 11 and 12 illustrate the reaction between magnets 22 installed around supply station 20 mounting index 21 and filter cassette stopper 15. To mount the filter cassette magazine 1, first, align the mounting slot with a mounting pin 23, insert it into the mounting index 21, and then rotate it in a clockwise or counter-clockwise direction until the magnet 22 and filter stopper magnet 16 are firmly engaged. As soon as magnets 22 pull stopper magnet 16, the filter cassette stopper moves in an outward direction and releases filter cassette(s) into the empty filter cassette carrier hole 63.

FIG. 13 through FIG. 16 show the filter cassette storage processes. The storage station 20 mounting index 21 doesn't have a pulling magnet. Therefore, the filter cassette stopper 15 is in a free position. After sampled filter F1 is carried into magazine storage station 20, storage station plunger 118 moves upward by lever system 120 (see FIG. 13). As the storage plunger 118 moves upwardly with filter cassette F3, filter cassette F3 pushes four filter cassette stoppers 15 outwardly in a radial direction (see FIG. 14). After the filter cassette F3 passes the filter cassette stopper 15 position, four filter cassette stoppers return to their free position (see FIG. 16). When the storage plunger 118 moves back downward, the four filter cassette stopper 15 hold filter cassette(s) F3, which is stored in the storage station 10 magazine 1. A reflectance sensor 170 senses the presence of the filter cassette F3. The detection distance limit of the reflectance sensor 170 is about one and half of the filter cassette thickness. If the filter cassette is secured by the filter cassette stoppers, reflectance sensor 170 treats there is no filter cassette F3 remaining in the storage station carrier hole 63 and allows gear motor to rotate the filter cassette carrier 51.

The term "ribbon" is here used to designate a piece of concave-convex form of thin flexible metal or plastic ribbon (like tape measure metal tape).

Figure 17:
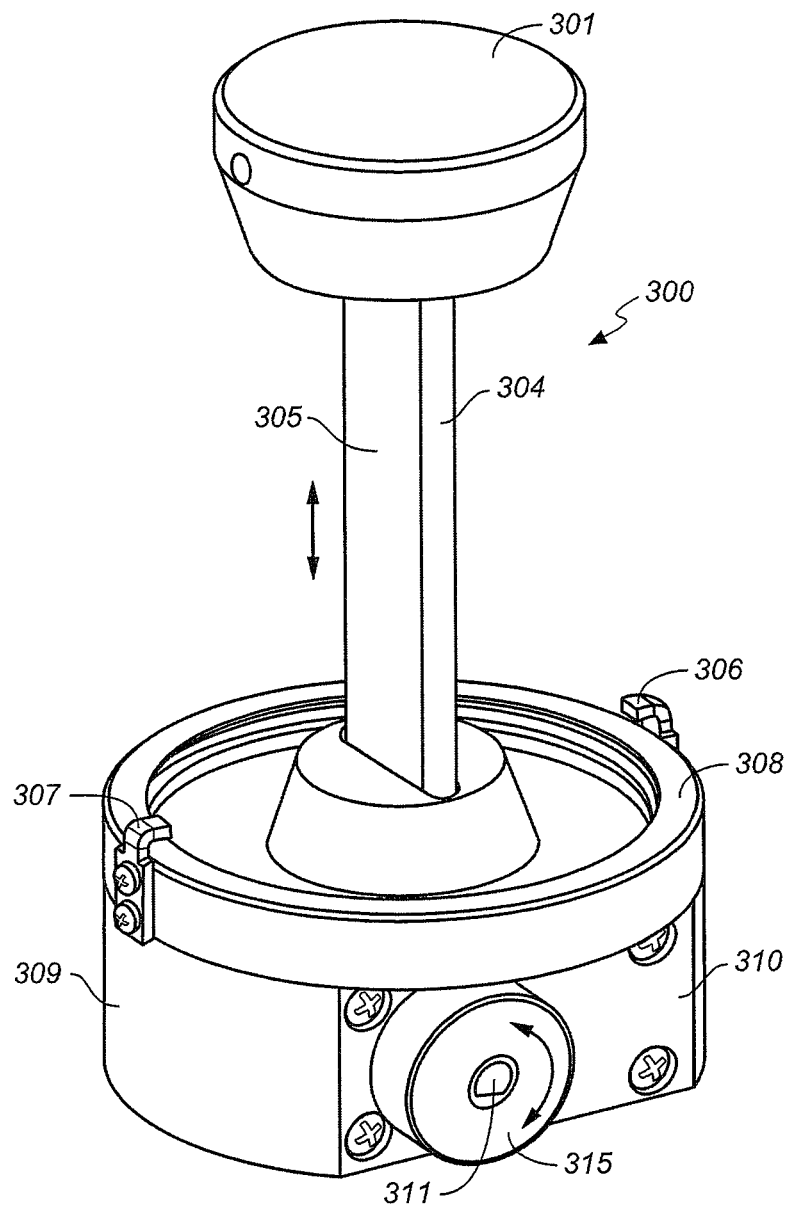
FIG. 17 shows perspective view of retaining lid 300.

FIG. 17 shows perspective view of retaining lid 300. A retaining lid 300 is used to cover bottom of the filter cassette magazine 1 and to secure new and used stack of filter cassettes F1s or F3s from shaking whenever the filter cassette magazine 1 is transferred place to place. A piston 301 is attached on top of ribbons 304 and 305 moves up and down with ribbons 304 and 305. Ribbons 304 and 305 contact face to face of the convex side to form a structural column.

Figure 18:
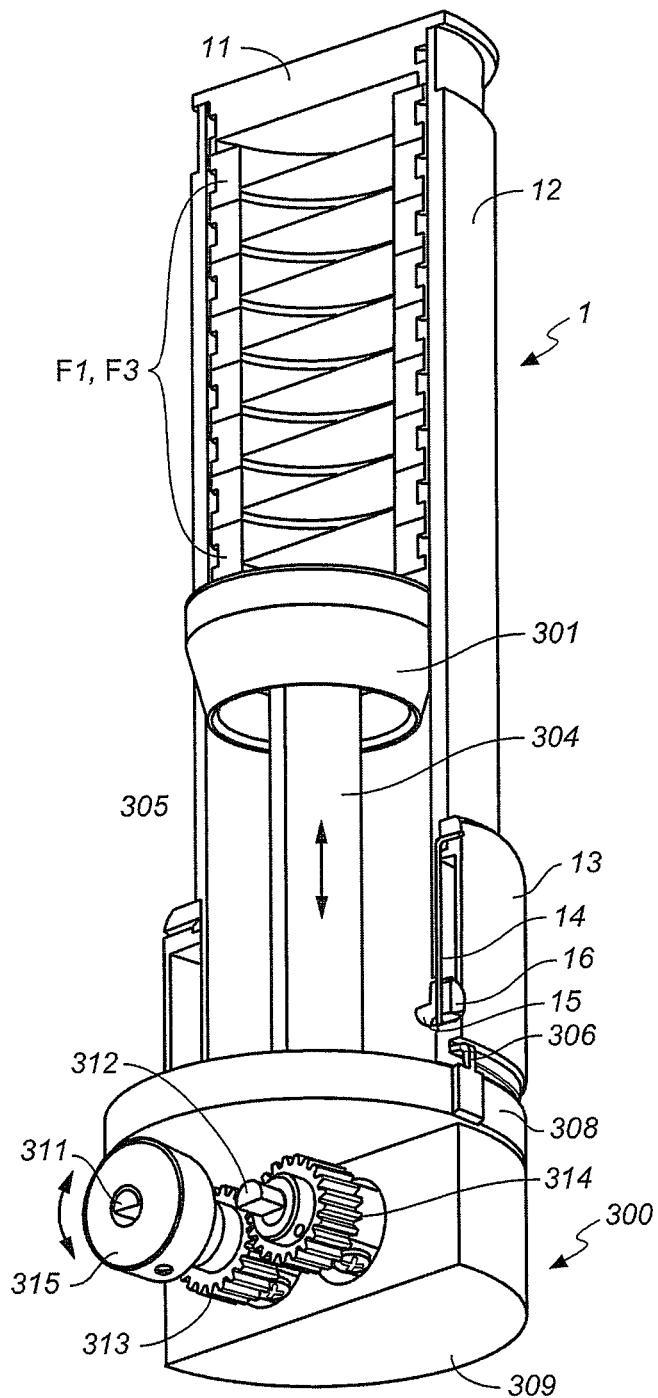
FIG. 18 shows illustrative embodiment of retaining lid 300 with cross cut view of filter cassette magazine 1.

FIG. 18 shows how the retaining lid 300 secures filter cassettes F1s or F3s from shaking inside the filter cassette magazine 1 whenever filter cassettes F1s or F3s do not fully fill the inside of the filter cassette magazine 1. By turning a knob 315 counter-clockwise, a piston 301 moves upward by two ribbons 304, 305. Ribbons 304 and 305 are wound on their own bobbin 312 and 311, respectively. Bobbin 311 and 312 are connected by gears 313 and 314. Therefore, bobbins 311 and 312 turn in opposite directions.

The retaining lid 300 is attached from the bottom of the filter cassette magazine and secured by hooks 306 and 307.

Figure 19:
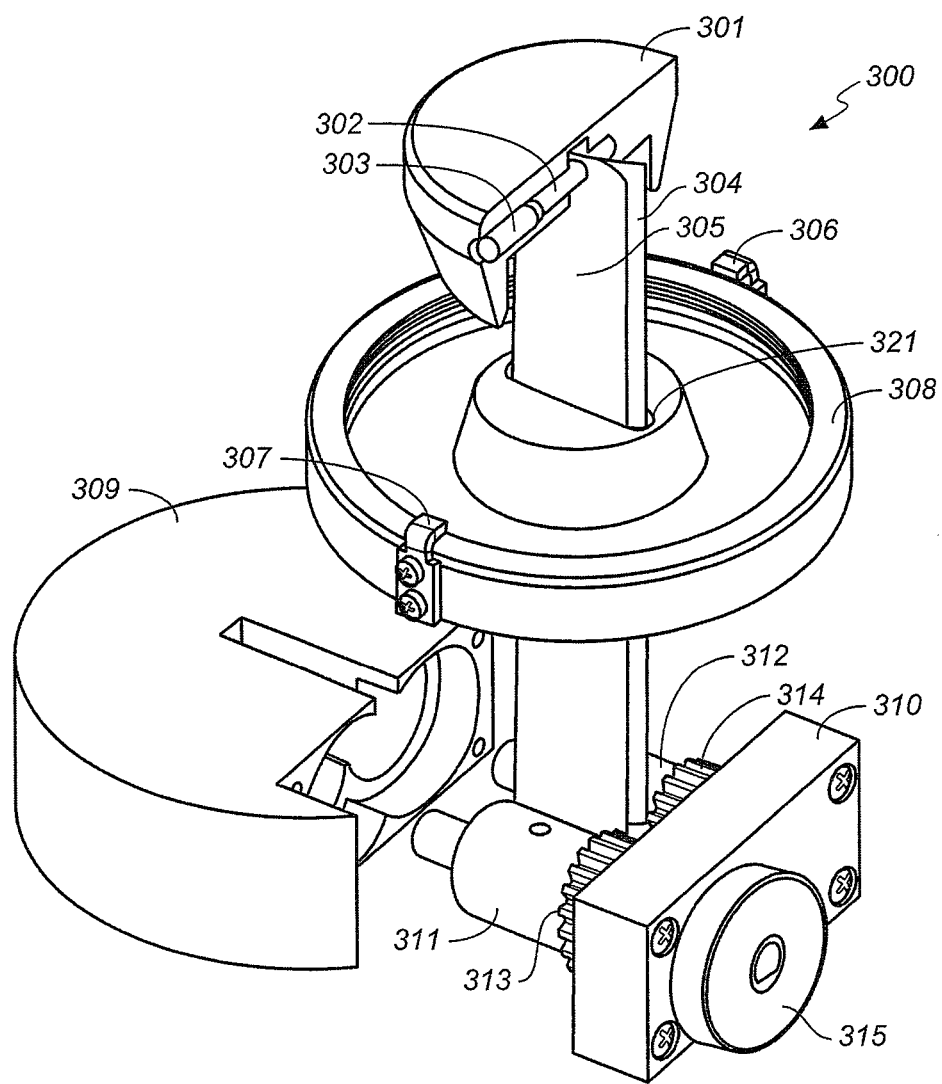
FIG. 19 is an expended perspective view of retaining lid 300.

FIG. 19 shows an exploded perspective view of the retaining lid 300. Piston 301 is connected with two ribbons with pin 302. Two ribbons 304, 305 slide through slot hole 321 in the middle of a sealing plate 308. The sealing plate 308 closes the bottom of the filter cassette magazine 1 and is secured by two hooks 306 and 307. A holding block 309 holds the bobbins 311, 312 and two gears 313, 314. A cover block 310 also supports bobbins 311, 312. Knob 315 is connected directly with bobbin 311.

Figure 20:
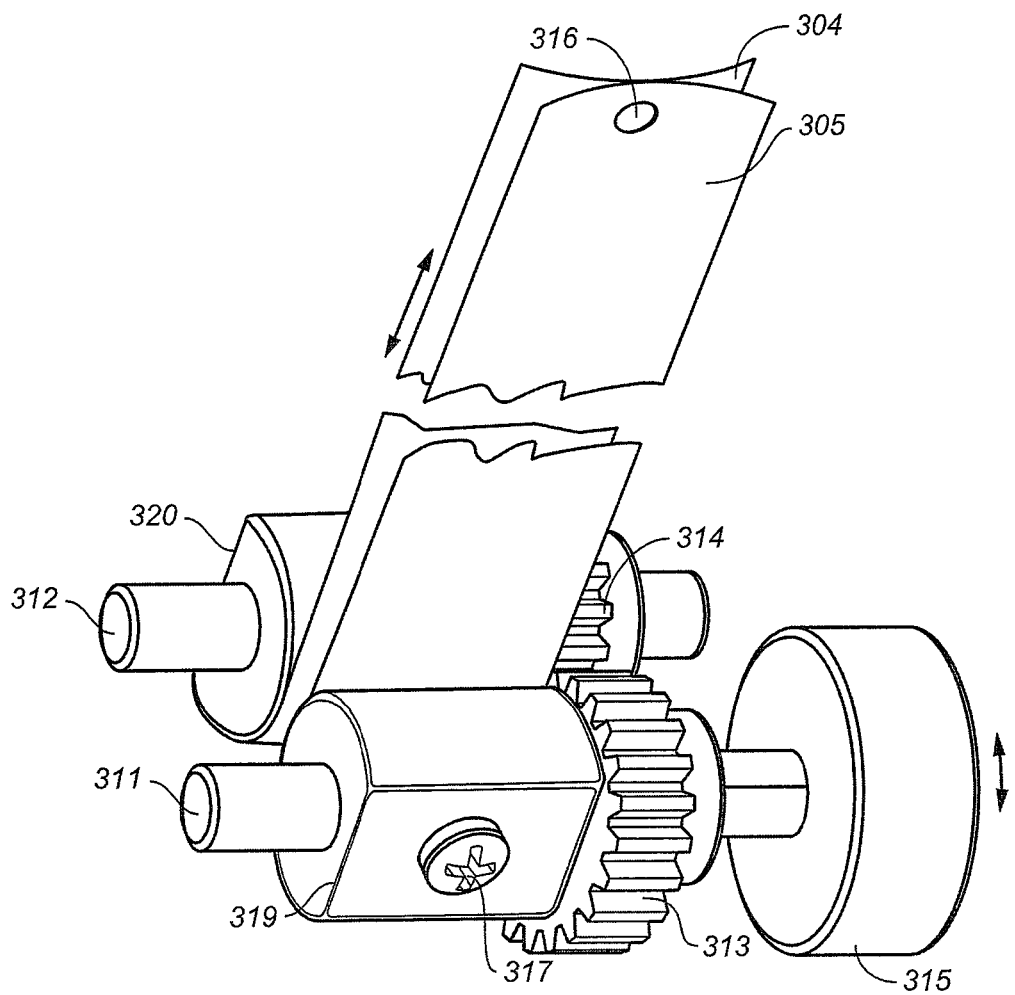
FIG. 20 shows illustrative embodiment of winding mechanism of retaining lid 300.

FIG. 20 shows a partial perspective view of winding mechanism. By rotating knob 315, bobbin 311 and gear 313 rotate in the same direction. Bobbin 312 rotates in the opposite direction simultaneously with gear 314. Formed ribbons 304 and 305 are secured with bobbins 312 and 311 respectively by screws 317 on the flat surface 319, 320 of bobbin 311 and 312 respectively.

What is claimed is:

1. A sequential air sampler, comprising:
  a rotatable carrier adapted to support filter cassettes and transport the cassettes between a series of stations including a sampling station;
  means for directing gas flow through a filter cassette when located at the sampling station;
  a supply magazine providing a stack of filter cassettes for loading onto the rotatable carrier at a load station;
  a storage magazine for receiving used filter cassettes at an unload station; and
  a mechanism for rotating the carrier between stations and driving simultaneous loading and unloading of filter cassettes at respective load and unload stations, the mechanism including a Geneva driver operated by a single motor providing intermittent rotation to the carrier between a set of fixed carrier positions such that a loaded cassette on the carrier is located at the sampling station, the mechanism also including a cam and follower associated with a pair of plungers at the sampling and unload stations, the cam rotating in concert with the Geneva driver so that the follower in reciprocating motion simultaneously pushes up the pair of plungers and then pulls down both plungers whenever the carrier has arrived at any of its fixed carrier positions.

2. The air sampler as in claim 1, wherein the respective supply and storage magazines are located above the carrier and have stoppers to keep cassettes in a stack within each magazine without falling out.

3. The air sampler as in claim 2, wherein stoppers are magnetically actuated to release one cassette from the supply magazine onto the carrier.

4. The air sampler as in claim 1, wherein the plungers are located beneath the carrier, a plunger associated with the unload station pushing up to place a used cassette from the carrier into the storage magazine.

5. The air sampler as in claim 4, wherein a sliding rod couples the follower to a lever system for the plungers so as to amplify follower travel distance into a larger displacement of the plungers.

6. The air sampler as in claim 1, wherein the carrier has four fixed positions spaced at equal 90 degree rotations relative to one another, the carrier further having four open hole receptacles for holding cassettes at the respective load, sampling and unload stations.

7. The air sampler as in claim 1, wherein the cam has a shape selected to provide a dwell period for the follower and plungers during the intermittent carrier rotation.

8. The air sampler as in claim 1, wherein there are two cams, a roller follower and a sliding rod connected to the roller follower by a connecting plate, the roller follower directly associated with a sampling station plunger and the sliding rod associated with a unload station plunger.

9. The air sampler as in claim 1, wherein each magazine received at the load and unload stations are equipped with a retaining lid to cover a magazine bottom for magazine transport.

10. The air sampler as in claim 9, wherein each magazine further has a position-adjustable piston attached to the retaining lid with the piston engaging a stack of cassettes so as to firmly secure the cassettes against shaking or displacement.

11. The air sampler as in claim 10, wherein the retaining lid of each magazine further has a piston attached on top of structurally-formed flexible ribbons that can wind onto a winding bobbin.

12. The air sampler as in claim 11, wherein the position-adjustable piston in the retaining lid of each magazine can travel at least twice the retaining lid housing height.

13. A method of operating a sequential air sampler, comprising:
  receiving a supply magazine filled with a stack of clean filter cassettes at a load station and a storage magazine that is initially empty at an unload station, both magazines received above an intermittently rotatable carrier adapted to support filter cassettes and transport the cassettes between the load station, a sampling station, and the unload station, the carrier operated by a Geneva driver operated by a single motor providing the intermittent rotation to the carrier between a set of fixed carrier positions, and a cam and follower associated with a pair of plungers at the sampling and unload stations, the cam rotating in concert with the Geneva driver so that the follower in reciprocating motion simultaneously pushes up the pair of plungers and then pulls down both plungers whenever the carrier has arrived at any of its fixed carrier positions;
  loading a filter cassette onto the carrier at the load station and subsequently transporting that cassette to the sampling station;
  directing gas flow through a filter cassette when located at the sampling station; and
  transporting used filter cassettes from the sampling station to the unload station and pushing it into the storage magazine;
  wherein simultaneously at each fixed carrier position a new cassette is loaded onto the carrier at the load station, previously loaded cassette samples the gas flow at the sampling station, and a used cassette is pushed into the storage magazine at the unload station.

* * * * *